United States Patent
Hsu et al.

(10) Patent No.: US 10,592,816 B1
(45) Date of Patent: Mar. 17, 2020

(54) QUANTUM COMPUTATION FOR OPTIMIZATION IN EXCHANGE SYSTEMS

(71) Applicant: Accenture Global Solutions Limited, Dublin (IE)

(72) Inventors: Kung-Chuan Hsu, Cerritos, CA (US); Marc Carrel-Billiard, Vence (FR); Max Howard, San Francisco, CA (US); Carl Matthew Dukatz, San Jose, CA (US); Kirby James Linvill, Santa Clara, CA (US); Shreyas Ramesh, Sunnyvale, CA (US)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/399,121

(22) Filed: Apr. 30, 2019

Related U.S. Application Data (60) Provisional application No. 62/774,479, filed on Dec. 3, 2018.

(51) Int. Cl.
  *G06N 10/00* (2019.01)
  *G06F 15/16* (2006.01)
  *G06F 17/11* (2006.01)

(52) U.S. Cl.
  CPC ............ *G06N 10/00* (2019.01); *G06F 15/16* (2013.01); *G06F 17/11* (2013.01)

(58) Field of Classification Search
  None
  See application file for complete search history.

(56) References Cited

U.S. PATENT DOCUMENTS

2017/0177544 A1* 6/2017 Zaribafiyan ............ G06N 5/003

OTHER PUBLICATIONS

Narimani, Ali Seyed Saeed Changiz Rezaei, and Arman Zaribafiyan. "Combinatorial Optimization by Decomposition on Hybrid CPU-non-CPU Solver Architectures" Sep. 16, 2017 [Online] Downloaded Sep. 5, 2019 https://arxiv.org/pdf/1708.03439.pdf (Year: 2017).*

Mak-Hau, Vicky. "On the kidney exchange problem: cardinality constrained cycle and chain problems on directed graphos: a survey of integer programming approaches" 2015 [Online] Downloaded Sep. 5, 2019 https://rd.springer.com/article/10.1007%2Fs10878-015-9932-4 (Year: 2015).*

(Continued)

*Primary Examiner* — Ben M Rifkin
(74) *Attorney, Agent, or Firm* — Fish & Richardson P.C.

(57) ABSTRACT

Methods, systems, and apparatus for improving exchange systems. In one aspect, a method includes receiving data representing an exchange problem; determining, from the received data, an integer programming formulation of the exchange problem; mapping the integer programming formulation of the exchange problem to a quadratic unconstrained binary optimization (QUBO) formulation of the exchange problem; obtaining data representing a solution to the exchange problem from a quantum computing resource; and initiating an action based on the obtained data representing a solution to the exchange problem.

18 Claims, 3 Drawing Sheets

(56) References Cited

OTHER PUBLICATIONS

Galati, Matthew. "The Kidney exchange problem" Feb. 6, 2015 [Online] Downloaded Sep. 4, 2019 https://blogs.sas.com/content/operations/2015/02/06/the-kidney-exchange-problem/ (Year: 2015).*
Marchenkova, Anastasia. "What's the difference between quantum annealing and universal gate quantum computers" Feb. 28, 2016 [Online] Downloaded Sep. 4, 2019 https://medium.com/quantum-bits/what-s-the-difference-between-quantum-annealing-and-universal-gate-quantum-computers-c5e5099175a1 (Year: 2016).*
Duffy "It's A Match: Algorithm Finds Kidneys" Carnegie Mellon, Futurity, Nov. 18, 2010.
Glorie et al. "Allocation and matching in kidney exchange programs" Wiley Online Library, Sep. 30, 2013, https://doi.org/10.1111/tri.12202l.
Malik et al. "State of the Art Practices and Policies in Kidney Paired Donation" Curr Transpl Rep (2014) 1:10-17.
Patel "I Gave My Kidney to a Stranger to Save My Brothers Life" The Wall Street Journal, Mar. 9, 2019.
Roth et al. "New Challenges in Multihospital Kidney Exchange" American Economic Review: Papers & Proceedings 2012, 102(3): 354-359, http://dx.doi.org/10.1257/aer.102.3.354.
Roughgarden "CS364A: Algorithmic Game Theory, Lecture #10: Kidney Exchange and Stable Matching" Stanford Univeresity, Oct. 23, 2013.

* cited by examiner

FIG. 3

QUANTUM COMPUTATION FOR OPTIMIZATION IN EXCHANGE SYSTEMS

CROSS-REFERENCE TO RELATED APPLICATION

This application claims the benefit under 35 U.S.C. § 119(e) of the filing date of U.S. Patent Application No. 62/774,479, for Improved Exchange Systems Using Quantum Computation, which was filed on Dec. 3, 2018, and which is incorporated here by reference in its entirety.

TECHNICAL FIELD

The present invention relates to quantum computing.

BACKGROUND

Exchange systems implement exchange programs where participants in a transaction directly exchange resources or services for other resources or services without using a medium of exchange, such as money.

One example exchange system is a system implementing a kidney transplant exchange program. Kidney transplants allow patients with kidney diseases to replace their non-functional kidneys with healthy kidneys from deceased or, preferably, living donors. In many countries organ-selling is prohibited and illegal, so a living donor is usually closely-related to the patient. However, even if a patient is able to find a donor willing to donate his or her kidney, it is often the case that the kidney is not compatible to the patient's body. If an incompatible kidney is transplanted, the patient's body can reject the organ, leading to a failure of the transplant.

The compatibility of a donor kidney and patient can be tested and confirmed with a certain level of confidence prior to the transplant. Then, if a patient-donor pair is found to be incompatible or not well-matched, the pair can join a kidney exchange program to swap donor kidneys with another potential patient-donor pair. The kidney exchange program therefore enables the frequent issue of incompatibility in kidney transplant to be overcome by swapping kidneys between a group of patient-donor pairs.

The concept of kidney exchange was initially outlined in 1986 by Felix Rapaport, and the first kidney exchange program was operated in 1991 in South Korea. Since then, the idea has been gradually adopted and performed throughout different parts of the World. Today, many compatible patient-donor pairs join kidney exchange programs for the purpose of searching for even better-matched kidneys. In 2015, the largest recorded kidney exchange was performed, which involved 34 patient-donor pairs and 26 different hospitals over the course of three months.

Due to the increasing popularity of kidney exchange, the size of kidney exchange programs is constantly growing. As described in this specification, allocating the swap of kidneys in a kidney exchange system is a combinatorial optimization problem, and it is NP-complete when certain restrictions are enforced. Therefore, efficient algorithms are needed for solving the kidney exchange optimization problem. Due to the NP-completeness of the kidney exchange problem, there is no efficient algorithm for solving the problem on a classical computer.

SUMMARY

This specification describes methods and systems for allocating items in an exchange system using quantum computing resources.

Quantum computing resources that utilize quantum mechanical phenomena to perform computations may be used to solve NP complete problems efficiently. Quantum computation has risen in popularity in recent years due to quantum annealing computers becoming commercially available and experimental breakthroughs in technologies such as superconducting quantum computing.

The field of quantum computing was initially introduced in the 1980s, notably by physicists such as Richard Feynman, David Deutsch, and Paul Benioff. Quantum computation, as opposed to classical computation with bit strings in a discrete and real vector space, uses quantum particles as computational resource, which can be described as states in a continuous vector space allowing complex amplitudes (Hilbert Space). The advantage of quantum computation comes from quantum-mechanical phenomena such as superposition and entanglement, that allow a quantum system to simultaneously be in different states and hold correlation within and with other quantum systems.

The field of quantum computing received particular attention in 1994 when Peter Shor proposed the first quantum algorithm—an algorithm for integer factorization—that demonstrated an exponential speedup compared to the best corresponding classical algorithm. This was an important discovery since the success of modern cryptography, such as the RSA cryptosystem, is due to the difficulty of factoring large composite integers. This proposal, and many other efficient quantum algorithms discovered afterwards, have demonstrated the potential of quantum computers.

In general, one innovative aspect of the subject matter described in this specification can be implemented in a method that includes receiving data representing an exchange problem; determining, from the received data, an integer programming formulation of the exchange problem; mapping the integer programming formulation of the exchange problem to a quadratic unconstrained binary optimization (QUBO) formulation of the exchange problem; obtaining data representing a solution to the exchange problem from a quantum computing resource; and initiating an action based on the obtained data representing a solution to the exchange problem.

Other implementations of this aspect include corresponding classical, quantum or classical-quantum computer systems, apparatus, and computer programs recorded on one or more computer storage devices, each configured to perform the actions of the methods. A system of one or more classical and quantum computers can be configured to perform particular operations or actions by virtue of having software, firmware, hardware, or a combination thereof installed on the system that in operation causes or cause the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination. In some implementations the integer programming formulation of the exchange problem to be solved comprises: an objective function to be maximized; and one or more constraints, comprising equality and inequality constraints.

In some implementations mapping the integer programming formulation of the exchange problem to a QUBO formulation of the exchange problem comprises: mapping the objective function to be maximized to a QUBO objective function to be minimized; and adding a penalty term to the QUBO objective function to be minimized, wherein the penalty term is determined based on the one or more constraints.

In some implementations the method further comprises determining the penalty term, comprising: for each equality constraint: representing the constraint as an equation equaling zero when the constraint is satisfied and equaling a strictly positive value when the constraint is not satisfied; multiplying the equation by a weight to generate a corresponding partial-penalty term; and including the generated partial-penalty terms in the penalty term.

In some implementations the method further comprises, for each inequality constraint: formulating the inequality constraint as an equality constraint comprising slack variables, wherein each slack variable is a binary variable; determining the penalty term using the equality constraint comprising slack variables.

In some implementations when the quantum computing resource comprises a quantum annealing computer, optionally wherein the solution to the exchange problem is computed using quantum adiabatic computation.

In some implementations when the quantum computing resource comprises a gate-based universal quantum computer, optionally wherein the solution to the exchange problem is computed using a Quantum Approximate Optimization Algorithm.

In some implementations the method further comprises performing classical post-processing of the data representing a solution to the exchange problem obtained from the quantum computing resource.

In some implementations initiating an action based on the obtained data representing a solution to the exchange problem comprises exchanging resources or services based on the solution to the exchange problem.

In some implementations the received data comprises data representing: exchange problem participants, wherein each participant offers resources or services in exchange for other resources or services without using a medium of exchange; constraints on exchanges between exchange problem participants; and the exchange problem to be solved.

In some implementations the exchange problem comprises a kidney exchange problem.

In some implementations the exchange problem participants comprise incompatible donor-recipient pairs, wherein each incompatible donor-recipient pair comprises (i) a donor willing to donate a kidney, and (ii) a patient in need of a donor kidney of a different type to that offered by the donor.

In some implementations constraints on exchanges between exchange problem participants comprise: a first constraint that ensures no kidney is donated more than once; a second constraint that ensures that a donor of an incompatible donor-recipient pair donates a kidney only if the patient in the incompatible donor-recipient pair receives a kidney from another donor.

In some implementations the kidney exchange problem to be solved comprises: modelling the kidney exchange problem as a graph of vertices and directed weighted edges, wherein vertices represent the incompatible donor-recipient pairs, edges represent compatible donor-recipient pairs; and edge weights represent a medical benefit of a compatible donor-recipient pair; and determining one or more disjoint cycles of donor-recipient pairs that increases overall medical benefits of associated kidney transplants.

In some implementations the number of donor-recipient pairs in each of the one or more disjoint cycles is below a predetermined threshold.

In some implementations initiating an action based on the obtained data representing a solution to the exchange problem comprises transplanting multiple kidneys based on the solution to the exchange problem.

The subject matter described in this specification can be implemented in particular ways so as to realize one or more of the following advantages. Exchange systems that utilize quantum computing resources, as described in this specification, can obtain solutions to exchange problems that are otherwise intractable for classical computing resources. For example, some exchange problems are NP-complete, e.g., due to constraints associated with the exchange problem. Since there are no efficient algorithms for solving NP-complete problems on a classical computer, conventional exchange systems cannot efficiently solve such exchange problems. However, by reformulating the exchange problem using the techniques described in this specification, the exchange problem can be provided to a quantum computing resource that has the processing capabilities to efficiently solve the exchange problem.

Exchange systems that utilize quantum computing resources, as described in this specification, can be applied to a variety of technical applications, including kidney exchange programs, digital platforms for trading goods and services, or programs for exchanging electrical energy between a micro grid and electric utility distribution network.

Using the kidney exchange problem as a specific example, in the United States alone it is estimated that more than 100,000 people are on a transplant list waiting for a kidney. These people can wait on average four to five years before a transplant. With such waiting periods, thousands of people per year die while waiting on the transplant list. When applied to the kidney exchange problem, the exchange systems described in this specification can be used to increase transplant numbers. In addition, patients can be better matched with donors. Increased compatibility of patient-donor organs may lead to a reduction in the amount of drugs ingested by the patient, e.g., cyclosporine derivatives, that prevent organ rejection. Patient healthcare can be improved and mortality rates reduced.

The details of one or more implementations of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes methods and systems for solving exchange problems, e.g., a kidney exchange problem, using quantum computing resources. A method for formulating the exchange problem as a quadratic unconstrained binary optimization (QUBO) problem is provided.

A quantum annealing computer can naturally solve the QUBO problem, and a gate-based universal quantum computer can utilize a Quantum Approximate Optimization Algorithm (QAOA) to efficiently search for good approximate solutions to the QUBO problem.

Figure 1:
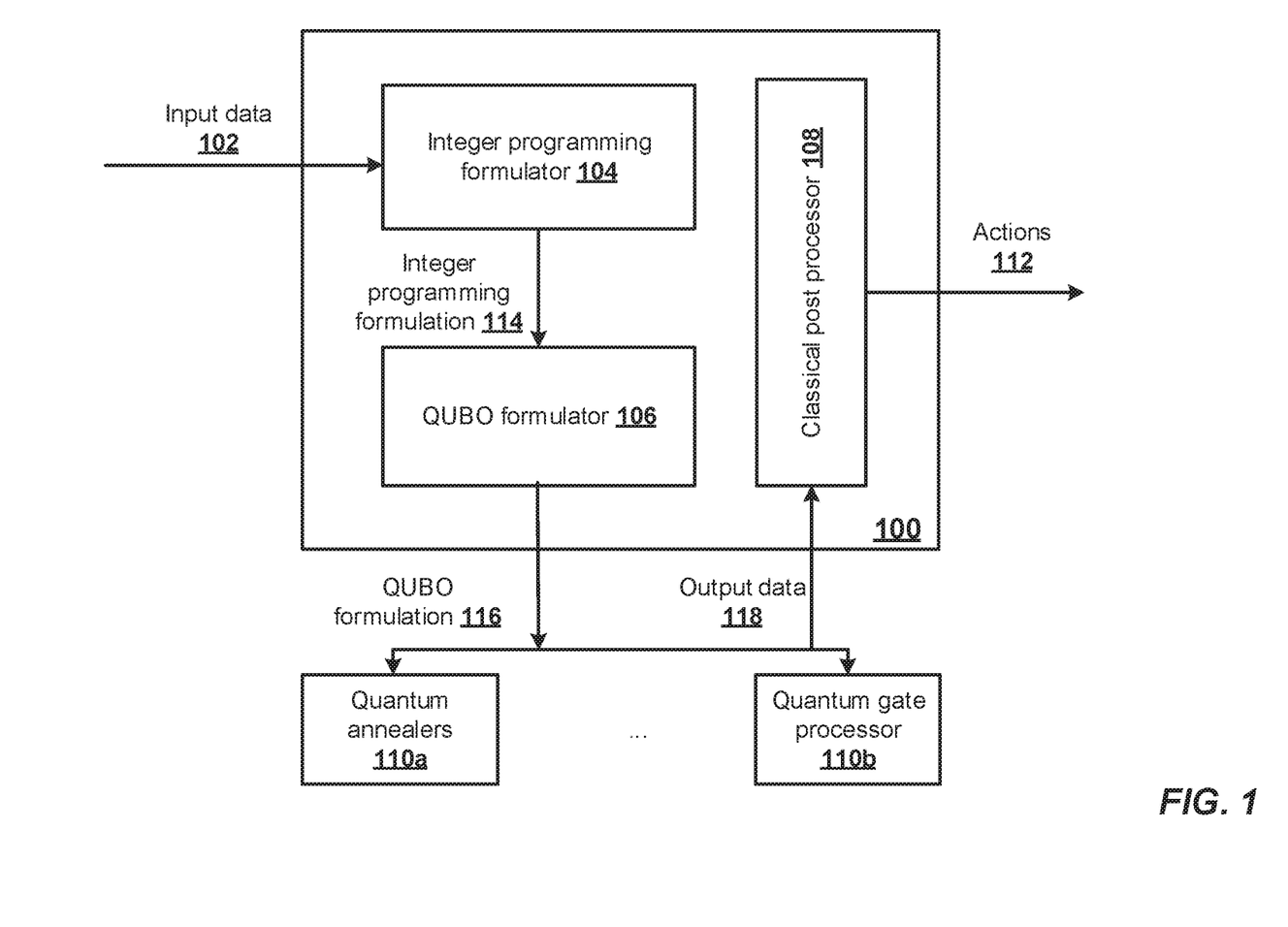
FIG. 1 shows an example system for implementing an exchange program.

FIG. 1 depicts an example system 100 for implementing an exchange program. The system 100 is an example of a system implemented as computer programs on one or more classical or quantum computing devices in one or more locations, in which the systems, components, and techniques described below can be implemented.

The system 100 includes an integer programming formulator 104, a QUBO formulator 106, a classical post-processor 108, and one or more quantum computing resources, e.g., quantum annealer 110a and quantum gate processor 110b. For convenience, two additional quantum computing resources are shown in FIG. 1, with the quantum computing resources being external to the system 100. However in some implementations the system 100 may be in communication with more or fewer additional quantum computing resources, or the system 100 may include the quantum computing resources. Components of the system 100 may be in data communication with each of the additional quantum computing resources, e.g., through a communication network such as a local area network or wide area network.

The system 100 is configured to receive as input data representing an exchange problem, e.g., input data 102. As described in more detail below with reference to step 202 of FIG. 2, the input data 102 may include data specifying the exchange problem to be solved. For example, the input data 102 may include data representing exchange problem participants, wherein each participant offers resources or services in exchange for other resources or services, e.g., without using a medium of exchange. The input data 102 may further include data representing constraints on exchanges between exchange problem participants.

The system 100 processes the received input data 102 to generate as output data representing actions to be initiated, e.g., actions 112. The actions are based on a determined solution to the exchange problem. For example, the actions may include an exchange of resources or services based on the solution to the exchange problem.

The system 100 is configured to determine a solution to the exchange problem represented by the input data 102. To determine a solution to the exchange problem, the system 100 uses one or more of the integer programming formulator 104, the QUBO formulator 106 or the classical post processor 108.

The integer programming formulator 104 is configured to receive the input data 102 and to process the received input data to determine an integer programming formulation 114 of the exchange problem represented by the input data 102. Example operations performed by the integer programming formulator 104 when processing received input data are described below with reference to FIG. 2.

The integer programming formulator 104 is configured to provide the determined integer programming formulation 114 of the exchange problem represented by the input data 102 to the QUBO formulator 106. The QUBO formulator 106 is configured to receive the integer programming formulation 114 of the exchange problem represented by the input data 102 and to map the integer programming formulation 114 of the exchange problem represented by the input data 102 to a quadratic unconstrained binary optimization (QUBO) formulation 116 of the exchange problem represented by the input data 102. Example operations performed by the QUBO formulator 106 to map a received integer programming formulation of an exchange problem are described below with reference to FIG. 2.

The system 100 is configured to transmit data representing the QUBO formulation 116 of the exchange problem represented by the input data 102 to one or more quantum computing resources. For example, the QUBO formulator 106 may directly provide the QUBO formulation 116 of the exchange problem to be solved to one or more quantum computing resources.

The quantum computing resources may include quantum annealer computing resources, e.g., quantum annealer 110a. A quantum annealer is a device configured to perform quantum annealing—a procedure for finding the global minimum of a given objective function over a given set of candidate states using quantum tunneling. Quantum tunneling is a quantum mechanical phenomenon where a quantum mechanical system overcomes localized barriers in the energy landscape which cannot be overcome by a classically described system. Some quantum annealer devices perform a subclass of quantum annealing called adiabatic quantum computing, which relies on the adiabatic theorem to perform computations.

Quantum annealer devices can solve problems if they are formulated in an acceptable format. For example, quantum annealer devices can solve some QUBO formulations of problems by mapping the QUBO formulation into a qubit network of a quantum annealer device.

The quantum computing resources may include one or more quantum gate processors, e.g., quantum gate processor 110b. A quantum gate processor includes one or more quantum circuits, i.e., models for quantum computation in which a computation is performed using a sequence of quantum logic gates, operating on a number of qubits (quantum bits).

Quantum gate processors can be used to solve certain optimization problems, e.g., problems that can be formulated as a QUBO problem. For example, some quantum gate processors can solve QUBO problems by simulating a corresponding adiabatic quantum annealing process using a gate model. This can be advantageous, e.g., compared to directly performing the corresponding adiabatic quantum annealing process using a quantum annealer device, since not all quantum annealer devices can realize physical quantum systems that represent an optimization problem. For example, some quantum annealer devices may not provide the physical interactions necessary to solve an optimization problem. In these examples, a Hamiltonian describing the optimization problem can be decomposed into a sequence of single or multi-qubit quantum gates, and a solution to the optimization problem can be obtained through application of the sequence of single or multi-qubit gates on a register of qubits and subsequent measurement of the register of qubits.

The one or more quantum computing resources that receive the transmitted data representing the QUBO formulation 116 of the exchange problem represented by the input data 102 are configured to process the received data to generate output data 118 representing a solution to the exchange problem. The one or more quantum computing resources are configured to provide the generated output data 118 to the system 100, e.g., to the classical post processor 108.

The system 100 is configured to receive the output data 118 from the one or more quantum computing resources. The classical post-processor 108 is configured to process the received output data 118. Processing the output data 118 may include determining one or more actions, e.g., exchanges of resources, to be taken based on the solution to the exchange problem.

The system 100 is configured to output data representing determined actions that can be taken 112. For example, the system 100 may provide the data 112 to, or include, a broker that initiates actions based on the output data.

Figure 2:
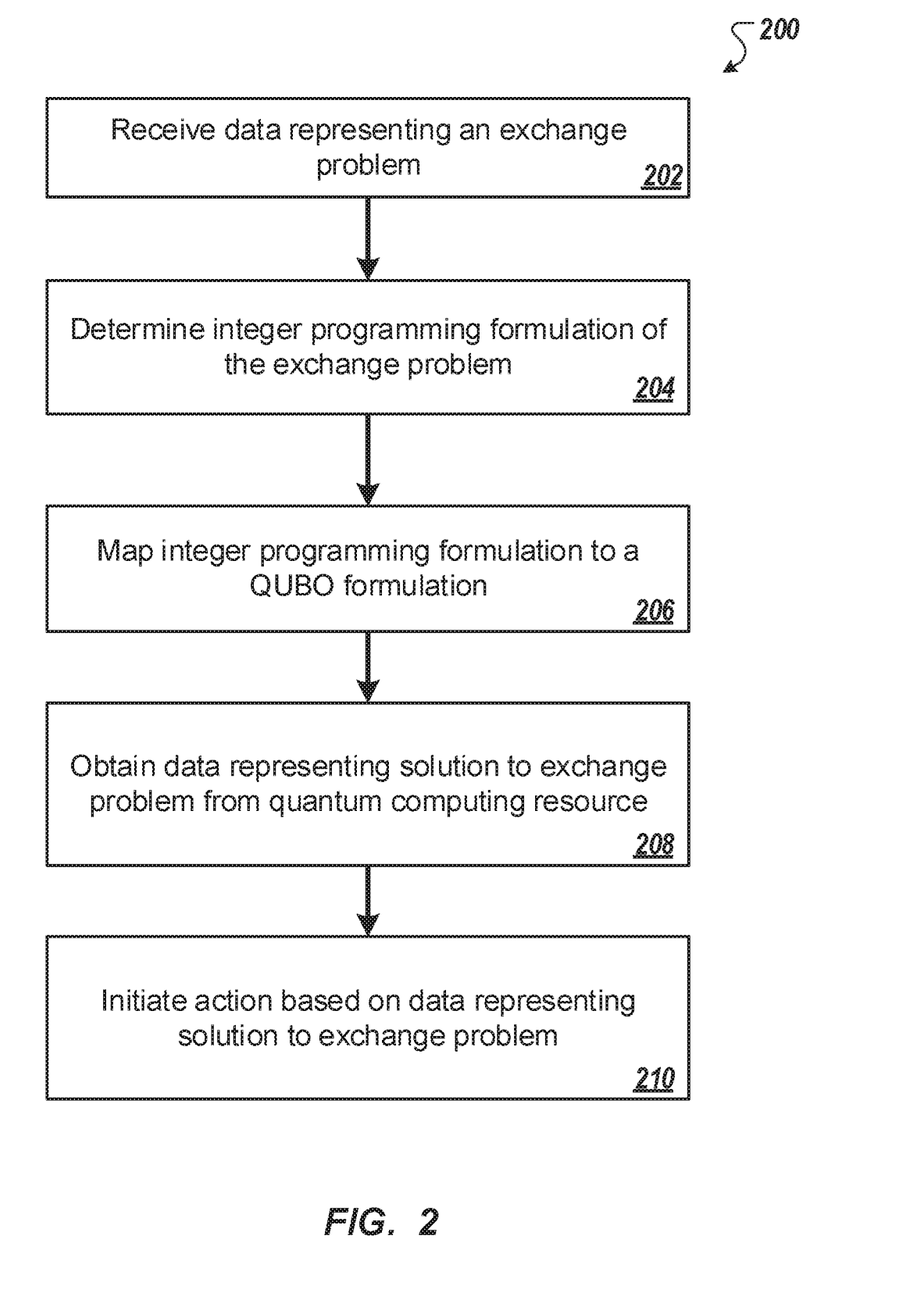
FIG. 2 is a flow diagram of an example process for solving an exchange problem using quantum computing resources.

FIG. 2 is a flowchart of an example process 200 for solving an exchange problem using quantum computing resources. For convenience, the process 200 will be described as being performed by a system of one or more classical or quantum computing devices located in one or more locations. For example, example system 100 of FIG. 1, appropriately programmed in accordance with this specification, can perform the process 200.

The system receives data representing an exchange problem (step 202). The received data may include data representing exchange problem participants, where each participant offers resources or services in exchange for other resources or services e.g., without using a medium of exchange. The received data may also include data representing constraints on exchanges between exchange problem participants. The received data may also include data specifying the exchange problem to be solved.

In some implementations the exchange problem may be a kidney exchange problem. In these implementations the exchange problem participants may include multiple donor-recipient pairs that include (i) a donor willing to donate a kidney, and (ii) a patient in need of a donor kidney. Donors and recipients can have different matching levels. For example, a donor in a first donor-recipient pair may have a high matching level with a recipient in a second donor-recipient pair if the kidney offered by the donor in the first pair is a same type or has other compatible characteristics with the recipient in the second pair, e.g., the chances of a successful transplantation (functionality with no organ rejection) is likely. Conversely, the donor in the first pair may have a lower matching level with a recipient in a third donor-recipient pair if the kidney offered by the donor in the first is a different type or has other incompatible characteristics, e.g., the chances of a successful transplantation is unlikely. If the chances of a successful plantation are very low, e.g., below a predetermined threshold, the donor-recipient pair may be referred to as an incompatible pair since the donor will never be allowed to donate a kidney to the recipient. In this specification, an incompatible donor-recipient pair refers to a donor-recipient pair with a low matching level.

In implementations where the exchange problem is a kidney exchange problem, the constraints on exchanges between exchange problem participants may include a first constraint that ensures no kidney is donated more than once. In addition, the constraints may further include a second constraint that ensures that a donor of a donor-recipient pair donates a kidney only if the patient in the incompatible donor-recipient pair receives a kidney from another donor.

In some implementations the system may model the received data representing the exchange problem as a graph. For example, the system may model the kidney exchange problem to be solved may be represented as a graph of vertices and directed weighted edges, where vertices represent the incompatible or not fully matched donor-recipient pairs, edges represent compatible or more fully matched donor-recipient pairs, and edge weights represent a medical benefit of a compatible or more fully matched donor-recipient pair. The system may also determine, from the graph, one or more disjoint cycles of donor-recipient pairs that increase overall medical benefits of associated kidney transplants. In some cases the number of donor-recipient pairs in each of the one or more disjoint cycles is below a predetermined threshold, e.g., a threshold determined based on available medical resources. For example, in some cases it may be too difficult to organize and synchronize the medical resources, e.g., surgeons, assistants, operating theatres, required to implement a kidney exchange for a large number of donor-recipient pairs.

For example, a kidney exchange network may be defined on a directed graph G(V, E), where each element $v_i$ in the vertex set $V=\{v_1, v_2, \ldots, v_n\}$ represents the i-th patient-donor pair in which the donor is willing to donate his/her incompatible kidney to the patient, and each element in the edge set E corresponds to an ordered pair (i, j), indicating a directional edge from vertex $v_i$ to vertex $v_j$. Denoting the edge of the pair (i, j) by $e_{i,j}$ and assuming that $e_{i,j}$ be in E if the patient of $v_i$ is body-type compatible with the donor of $v_j$ gives:

$$E=\{e_{i,j} | \text{patient of } v_i \text{ is body-type compatible with the donor of } v_j, 1 \leq i,j \leq n\} \quad (1)$$

The edges of the graph defined by the system may be weighted edges. There may be different weights assigned to different edges, where the weights of the edges represent the utility or priority of each individual transplant. In this specification, $w_{i,j}$ represents the weight of the edge $e_{i,j}$, where $w_{i,j} >> 0$ due to positive utilities, and C represents the set of cycles in G(V, E), where each $c \in C$ is the set of all vertices in the cycle. A cycle represents a successful kidney exchange involving the patient-donor pairs in the cycle.

The goal of the kidney exchange problem on G(V, E) is to find a set of disjoint (since each patient-donor pair can only donate one kidney and receive one kidney) cycles $C^* \subset C$ (which are called a "match") such that $f(C^*)=\Sigma_{c \in C^*} \Sigma_{e_{i,j} \in \epsilon(c)} w_{i,j}$, which is the sum of the weights of all edges covered by $C^*$, is maximized. Note that $\epsilon(c)$ is defined to be the set of all edges covered by the cycle c. Therefore, the optimization problem represented by the data received in step 202 may be given by:

$$\max_{C^* \subset C} f(C^*), \quad (2)$$

conditioned on the constraint $$c \cap d = \emptyset, \forall c, d \in C^*. \quad (3)$$

The system determines, from the received data, an integer programming formulation of the exchange problem (step 204). The integer programming formulation of the exchange problem to be solved may include an objective function to be maximized and one or more constraints, including equality and inequality constraints. An example of an integer programming formulation of the kidney exchange problem is described below.

Kidney Exchange Problem as an Example Integer Programming Problem

To map the kidney exchange problem above to an integer programming problem, the system introduces the following variables. For any instance of a matching $C^*$, let $x_{i,j}=1$ if and only if $e_{i,j} \in E$ and $e_{i,j}$ is covered by a cycle in $C^*$, else $x_{i,j}=0$. Note that in any matching, $x_{i,j}$ is always 0 if the edge $e_{i,j}$ does not exist (that is, $e_{i,j} \notin E$); therefore, these variables can be neglected in the end. The following description retains them for now to simplify the analysis.

The following is an example integer programming problem that solves the kidney exchange problem:

$$\max_{x_{i,j} \in \{0,1\}} \sum_{\substack{i,j \\ e_{i,j} \in E}} w_{i,j} \cdot x_{i,j}, \qquad (4)$$

with respect to the constraints $$x_{i,j} = 0, \forall e_{i,j} \notin E, \qquad (5)$$

$$\sum_j x_{i,j} = \sum_j x_{j,i}, \forall\, 1 \le i \le n, \qquad (6)$$

$$\sum_j x_{i,j} \le 1, \forall\, 1 \le i \le n. \qquad (7)$$

Equation (5) guarantees that $x_{i,j}=0$ whenever there is no edge from $v_i$ to $v_j$. equations (6) and (7) are to make sure that each vertex has an incoming edge and an outgoing edge when it is in a cycle (that there is no discontinuity in a path to form a cycle), and that each vertex is traversed at most once (that all cycles are disjoint).

Figure 3:
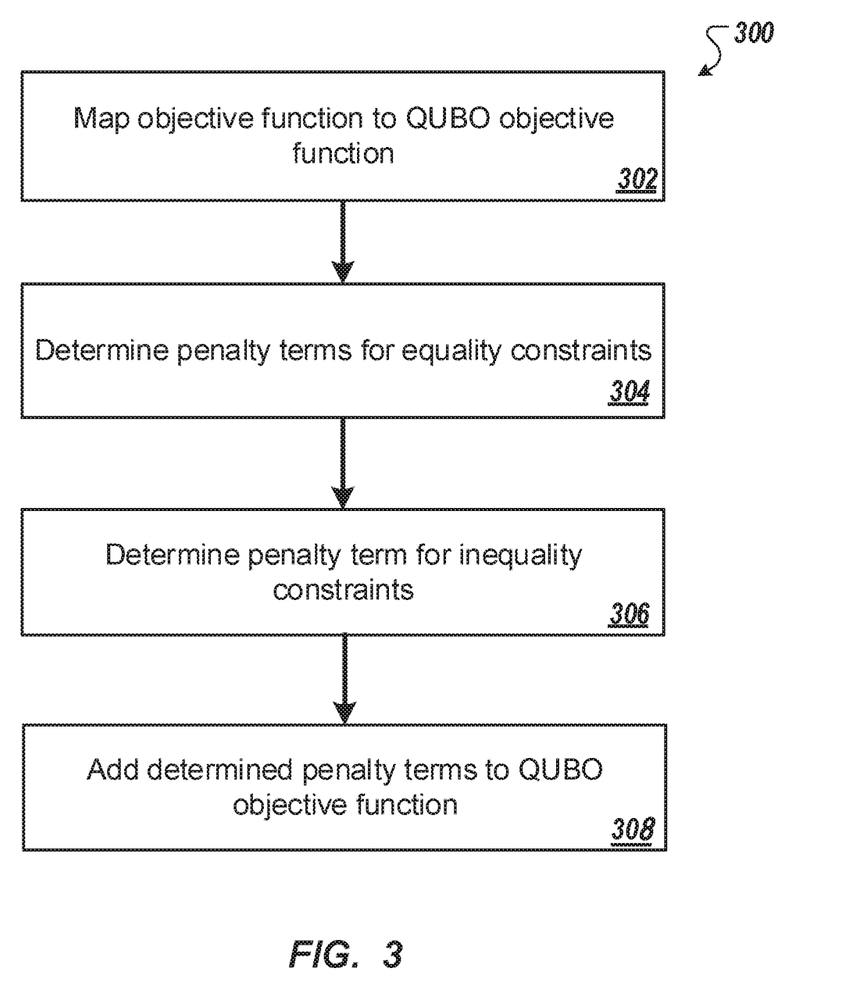
FIG. 3 is a flow diagram of an example process for mapping an integer programming formulation of an exchange problem to a QUBO formulation of the exchange problem.

The system maps the integer programming formulation of the exchange problem to a quadratic unconstrained binary optimization (QUBO) formulation of the exchange problem (step 206). FIG. 3 is a flow diagram of an example process 300 for mapping an integer programming formulation of an exchange problem to a QUBO formulation of the exchange problem. For convenience, the process 300 will be described as being performed by a system of one or more classical or quantum computing devices located in one or more locations. For example, example system 100 of FIG. 1, appropriately programmed in accordance with this specification, can perform the process 200.

The system maps the objective function to be maximized to a QUBO objective function to be minimized (step 302). The system adds a penalty term to the QUBO objective function to be minimized, where the penalty term is determined based on the one or more constraints (step 308).

In some implementations the system determines the penalty term. This may include determining penalty terms for equality constraints and inequality constraints in the integer programming formulation of the exchange problem (steps 304 and 306).

Determining penalty terms for the equality constraints (step 304) may include, for each equality constraint: representing the constraint as an equation equaling zero when the constraint is satisfied and equaling a strictly positive value when the constraint is not satisfied, multiplying the equation by a weight to generate a corresponding partial-penalty term and including the generated partial-penalty terms in the penalty term.

Determining penalty terms for the inequality constraints (step 306) may include formulating the inequality constraint as an equality constraint that includes slack variables, where each slack variable is a binary variable, and determine the penalty term using the equality constraint including slack variables as described above.

Mapping the integer programming formulation of the kidney exchange problem given by equations (4)-(7) to a quadratic unconstrained binary optimization (QUBO) formulation of the exchange problem is described below.

Example Mapping Reduction to a QUBO Problem

Recall that the objective function of a QUBO problem takes the form:

$$g(x) = x^T M x, \qquad (8)$$

where x represents a column vector with binary variables $x_1, x_2 \ldots$, and M represents a given symmetric matrix. Therefore, by expanding the above equation (8), it can be written in the following form containing only quadratic terms:

$$g(x) = \sum_i M_{i,i} x_i^2 + \sum_{i<j} 2 M_{i,j} x_i x_j. \qquad (9)$$

Equation (9) can also be written as $$g(x) = \sum_i M_{i,i} x_i + \sum_{i<j} (2 M_{i,j}) x_i x_j, \qquad (10)$$

since $x^2 = x_i$, due to $x_i$ being binary. Here, there are only linear and quadratic cross-terms.

The standard form of a QUBO problem is a minimization of the objective function. Therefore, equation (4) can be written in its QUBO standard form as:

$$\max_{x_{i,j} \in \{0,1\}} \sum_{\substack{i,j \\ e_{i,j} \in E}} -w_{i,j} \cdot x_{i,j}. \qquad (11)$$

When the data received by the system includes an equality constraint, e.g., B=c where B represents a function of the variables, a large-enough penalty is added to the objective function such that B>c or B<c are not allowed. That is, $W \cdot (B-c)^2$ can be added to the objective function. Since $(B-c)^2$ in this case is either 0 or $\ge 1$ due to equations (5)-(7) involving only binary variables and integer coefficients, W can be chosen large enough so that there is a large penalty to pay when a constraint is not satisfied. For example, W could be chosen to equal $$W = \sum_{\substack{i,j \\ e_{i,j} \in E}} w_{i,j} + \delta, \text{ where } \delta > 0, \qquad (12)$$

so that when a constraint is not satisfied, it would impose a positive penalty in the magnitude of $\ge W$, that is greater than $\sum_{e_{i,j} \in E} w_{i,j} \cdot x_{i,j}$, which is any instance of the objective function in equation (11).

That is, considering the new objective function with penalty $$\sum_{\substack{i,j \\ e_{i,j} \in E}} -w_{i,j} \cdot x_{i,j} + W \cdot (B-c)^2, \qquad (13)$$

when a constraint is not satisfied, the new objective function will have a value >0, and therefore would not be at minimum value since the trivial allocation (the instance of no exchange, where $x_i=0$ for all i) gives a value of 0.

Using the idea detailed above, the constraints given by equations (5)-(7) can be incorporated into the objective function equation (11), as follows.

For the constraint given by equation (5), for each pair of (i,j) where there is no edge from $v_i$ to $v_j$, add a penalty of $$W x_{i,j}^2 = W x_{i,j}. \qquad (14)$$

For the constraint given by equation (6), for each $i \in \{1, 2, \ldots, n\}$, add a penalty of W times $$\left(\sum_j x_{i,j} - \sum_j x_{j,i}\right)^2 = \left(\sum_j x_{i,j}\right)^2 + \left(\sum_j x_{j,i}\right)^2 - 2\sum_{j,k} x_{i,j} x_{k,i} = \qquad (15)$$

$$\sum_j (x_{i,j} + x_{j,i}) + 2\sum_{k<j}(x_{k,i} x_{j,i} + x_{i,k} x_{i,j}) - 2\sum_{j,k} x_{i,j} x_{k,i}.$$

For the constraint given by equation (7), the procedure is more complicated because the constraints are inequalities rather than equalities. A typical way of mapping inequality constraints to equality constraints is to introduce "slack" variables. For each $i \in \{1, 2, \ldots, n\}$, introduce a new binary variable $$y_i \in \{0,1\}. \qquad (16)$$

Recalling that the inequality constraint from equation (7) is $$\Sigma_j x_{i,j} \leq 1. \qquad (17)$$

The constraint given below in equation (18) is an equivalent constraint to that given by equation (17)

$$\Sigma_j x_{i,j} - y_i = 0, y_i \in \{0,1\}. \qquad (18)$$

Result: For fixed i, let $y_i \in \{0, 1\}$ be a free variable, then the constraint
$\Sigma_j x_{i,j} \leq 1$ is equivalent to the constraint $\Sigma_j x_{i,j} - y_i = 0$.
Proof of Result: To show that both constraints are equivalent, it is proven that they imply one another.
First of all, let $\Sigma_j x_{i,j} \leq 1$ be satisfied. Then since $x_{i,j} \geq 0$, $0 \leq \Sigma_j x_{i,j} \leq 1$. Hence, $\Sigma_j x_{i,j} = 0$ or 1, and $y_i$ can be chosen to be 0 or 1, respectively, so that $\Sigma_j x_{i,j} - y_i = 0$.
To show the converse, let $\Sigma_j x_{i,j} - y_i = 0$ be satisfied. Since $y_i \leq 1$, $\Sigma_j x_{i,j} = y_i \leq 1$. (Q.E.D.)
Therefore, by introducing binary variables $\{y_i\}_1^n$, the constraints in equation (7) may be rewritten as $$\sum_j x_{i,j} = y_i, \forall i \in \{1, 2, \ldots, n\}. \qquad (19)$$

For each of those constraints, add a penalty of W times $$\left(\sum_j x_{i,j} - y_i\right)^2 = \left(\sum_j x_{i,j}\right)^2 + y_i^2 - 2\sum_j y_i x_{i,j} = \qquad (20)$$

$$\sum_j x_{i,j} + 2\sum_{k<j} x_{i,j} x_{i,k} + y_i - 2\sum_j y_i x_{i,j}.$$

From equations (14), (15), and (20), the total penalty that should be added to the objective function is $W \cdot F(X, y)$, where X is the n×n matrix with elements $x_{i,j}$ and y is the n-vector with elements $y_i$, where $$F(X, y) = \sum_{\substack{i,j \\ e_{i,j} \in E}} x_{i,j} + 3\sum_{i,j} x_{j,i} + \sum_i y_i + \qquad (21)$$

$$4\sum_{\substack{i \\ k<j}} x_{i,j} x_{i,k} + 2\sum_{\substack{i \\ k<j}} x_{k,i} x_{j,i} - 2\sum_{i,j,k} x_{i,j} x_{k,i} - 2\sum_{i,j} y_i x_{i,j}.$$

Finally, the objective function in standard QUBO form is $$\sum_{\substack{i,j \\ e_{i,j} \notin E}} -w_{i,j} \cdot x_{i,j} + W \cdot F(X, y), \qquad (22)$$

where $F(X, y)$ is given by equation (21).

Equation (22) gives the QUBO coefficients for the linear terms $x_{i,j}$'s and $y_i$'s as well as their product (quadratic) terms. The coefficient matrix M for this QUBO problem can therefore be computed (see equation 8). The dimension (or number) of the variables is $|V|^2 + |v|$ at first glance, but since the variables $x_{i,j} = 0$ for $e_{i,j} \notin E$, the variables $x_{i,j}$ where $e_{i,j} \notin E$ can be removed. The effect of this on M is to remove all the rows and columns corresponding to those variables. The dimension of the variables is now $$d = |E| + |V| << |V|^2 + |V|. \qquad (23)$$

The solution is the $x_{i,j}$'s when the objective function is minimized.

In some implementations, for practicality, there may be an extra desired constraint, which is a fixed upper bound on the length of a cycle. This is due to the fact that a kidney exchange is much more difficult to perform when involving too many parties.

One solution to this, is to decrease all edge weights $w_{i,j}$ by an appropriate amount $\epsilon > 0$ such that all new weights $w_{i,j}^* = (w_{i,j} - \epsilon)$'s stay positive. Observing the first term in equation (22) when replacing w's with w*'s, a cycle of length m, compared to one with length n<m, will have an additional penalty of $(m-n)\epsilon > 0$. Therefore, this additional penalty for long cycles will render the solver favor short cycles. Note that the quality of the solution may be sensitive to the choice of $\epsilon$, and may be heavily dependent on the weight distribution and other problem settings.

Returning to FIG. 2, the system provides the QUBO formulation of the exchange problem to a quantum computing resource. The system obtains data representing a solution to the exchange problem from a quantum computing resource (step 208). In some implementations the quantum computing resource may be a quantum annealing computer. In these implementations the solution to the exchange problem may be computed using quantum adiabatic computation. In other implementations the quantum computing resource may be a gate-based universal quantum computer. In these implementations the solution to the exchange problem may be computed using a Quantum Approximate Optimization Algorithm or other quantum-classical hybrid variational algorithm.

In some implementations the system may perform classical post-processing of the data representing a solution to the exchange problem obtained from the quantum computing resource. In the QUBO formulation given by equation (22) above, the classical post-processing may include application of identity operators on $x_{i,j}$ variables and neglecting the y variables.

The system initiates an action based on the obtained data representing a solution to the exchange problem (step 210). Initiating an action may include initiating an exchange of resources or services based on the solution to the exchange problem. For example, when the exchange problem is the kidney exchange problem, initiating an action may include initiating transplantation of multiple kidneys based on the solution to the exchange problem.

Implementations of the digital and/or quantum subject matter and the digital functional operations and quantum operations described in this specification can be implemented in digital electronic circuitry, suitable quantum circuitry or, more generally, quantum computational systems, in tangibly-embodied digital and/or quantum computer software or firmware, in digital and/or quantum computer hardware, including the structures disclosed in this specification and their structural equivalents, or in combinations of one or more of them. The term "quantum computing device" may include, but is not limited to, quantum computers, quantum information processing systems, quantum cryptography systems, or quantum simulators.

Implementations of the digital and/or quantum subject matter described in this specification can be implemented as one or more digital and/or quantum computer programs, i.e., one or more modules of digital and/or quantum computer program instructions encoded on a tangible non-transitory storage medium for execution by, or to control the operation of, data processing apparatus. The digital and/or quantum computer storage medium can be a machine-readable storage device, a machine-readable storage substrate, a random or serial access memory device, one or more qubits, or a combination of one or more of them. Alternatively or in addition, the program instructions can be encoded on an artificially-generated propagated signal that is capable of encoding digital and/or quantum information, e.g., a machine-generated electrical, optical, or electromagnetic signal, that is generated to encode digital and/or quantum information for transmission to suitable receiver apparatus for execution by a data processing apparatus.

The terms quantum information and quantum data refer to information or data that is carried by, held or stored in quantum systems, where the smallest non-trivial system is a qubit, i.e., a system that defines the unit of quantum information. It is understood that the term "qubit" encompasses all quantum systems that may be suitably approximated as a two-level system in the corresponding context. Such quantum systems may include multi-level systems, e.g., with two or more levels. By way of example, such systems can include atoms, electrons, photons, ions or superconducting qubits. In many implementations the computational basis states are identified with the ground and first excited states, however it is understood that other setups where the computational states are identified with higher level excited states are possible. The term "data processing apparatus" refers to digital and/or quantum data processing hardware and encompasses all kinds of apparatus, devices, and machines for processing digital and/or quantum data, including by way of example a programmable digital processor, a programmable quantum processor, a digital computer, a quantum computer, multiple digital and quantum processors or computers, and combinations thereof. The apparatus can also be, or further include, special purpose logic circuitry, e.g., an FPGA (field programmable gate array), an ASIC (application-specific integrated circuit), or a quantum simulator, i.e., a quantum data processing apparatus that is designed to simulate or produce information about a specific quantum system. In particular, a quantum simulator is a special purpose quantum computer that does not have the capability to perform universal quantum computation. The apparatus can optionally include, in addition to hardware, code that creates an execution environment for digital and/or quantum computer programs, e.g., code that constitutes processor firmware, a protocol stack, a database management system, an operating system, or a combination of one or more of them.

A digital computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a digital computing environment. A quantum computer program, which may also be referred to or described as a program, software, a software application, a module, a software module, a script, or code, can be written in any form of programming language, including compiled or interpreted languages, or declarative or procedural languages, and translated into a suitable quantum programming language, or can be written in a quantum programming language, e.g., QCL or Quipper.

A digital and/or quantum computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A digital and/or quantum computer program can be deployed to be executed on one digital or one quantum computer or on multiple digital and/or quantum computers that are located at one site or distributed across multiple sites and interconnected by a digital and/or quantum data communication network. A quantum data communication network is understood to be a network that may transmit quantum data using quantum systems, e.g. qubits. Generally, a digital data communication network cannot transmit quantum data, however a quantum data communication network may transmit both quantum data and digital data.

The processes and logic flows described in this specification can be performed by one or more programmable digital and/or quantum computers, operating with one or more digital and/or quantum processors, as appropriate, executing one or more digital and/or quantum computer programs to perform functions by operating on input digital and quantum data and generating output. The processes and logic flows can also be performed by, and apparatus can also be implemented as, special purpose logic circuitry, e.g., an FPGA or an ASIC, or a quantum simulator, or by a combination of special purpose logic circuitry or quantum simulators and one or more programmed digital and/or quantum computers.

For a system of one or more digital and/or quantum computers to be "configured to" perform particular operations or actions means that the system has installed on it software, firmware, hardware, or a combination of them that in operation cause the system to perform the operations or actions. For one or more digital and/or quantum computer programs to be configured to perform particular operations or actions means that the one or more programs include instructions that, when executed by digital and/or quantum data processing apparatus, cause the apparatus to perform the operations or actions. A quantum computer may receive instructions from a digital computer that, when executed by the quantum computing apparatus, cause the apparatus to perform the operations or actions.

Digital and/or quantum computers suitable for the execution of a digital and/or quantum computer program can be based on general or special purpose digital and/or quantum processors or both, or any other kind of central digital and/or quantum processing unit. Generally, a central digital and/or quantum processing unit will receive instructions and digital and/or quantum data from a read-only memory, a random access memory, or quantum systems suitable for transmitting quantum data, e.g. photons, or combinations thereof.

The essential elements of a digital and/or quantum computer are a central processing unit for performing or executing instructions and one or more memory devices for storing instructions and digital and/or quantum data. The central processing unit and the memory can be supplemented by, or incorporated in, special purpose logic circuitry or quantum simulators. Generally, a digital and/or quantum computer will also include, or be operatively coupled to receive digital and/or quantum data from or transfer digital and/or quantum data to, or both, one or more mass storage devices for storing digital and/or quantum data, e.g., magnetic, magneto-optical disks, optical disks, or quantum systems suitable for storing quantum information. However, a digital and/or quantum computer need not have such devices.

Digital and/or quantum computer-readable media suitable for storing digital and/or quantum computer program instructions and digital and/or quantum data include all forms of non-volatile digital and/or quantum memory, media and memory devices, including by way of example semiconductor memory devices, e.g., EPROM, EEPROM, and flash memory devices; magnetic disks, e.g., internal hard disks or removable disks; magneto-optical disks; CD-ROM and DVD-ROM disks; and quantum systems, e.g., trapped atoms or electrons. It is understood that quantum memories are devices that can store quantum data for a long time with high fidelity and efficiency, e.g., light-matter interfaces where light is used for transmission and matter for storing and preserving the quantum features of quantum data such as superposition or quantum coherence.

Control of the various systems described in this specification, or portions of them, can be implemented in a digital and/or quantum computer program product that includes instructions that are stored on one or more non-transitory machine-readable storage media, and that are executable on one or more digital and/or quantum processing devices. The systems described in this specification, or portions of them, can each be implemented as an apparatus, method, or system that may include one or more digital and/or quantum processing devices and memory to store executable instructions to perform the operations described in this specification.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method comprising:
   receiving data representing an exchange problem;
   determining, from the received data, an integer programming formulation of the exchange problem, the integer programming formulation of the exchange problem comprising: i) an objective function to be maximized, ii) one or more constraints comprising equality and inequality constraints;
   mapping the integer programming formulation of the exchange problem to a quadratic unconstrained binary optimization (QUBO) formulation of the exchange problem, comprising:
      mapping the objective function to be maximized to a QUBO objective function to be minimized:
      determining a penalty term, comprising, for each equality constraint:
         representing the constraint as an equation equaling zero when the constraint is satisfied and equaling a strictly positive value when the constraint is not satisfied;
         multiplying the equation by a weight to generate a corresponding partial-penalty term; and
         including the generated partial-penalty terms in the penalty term; and
      adding the penalty term to the QUBO objective function to be minimized;
   obtaining data representing a solution to the exchange problem from a quantum computing resource; and
   initiating an action based on the obtained data representing a solution to the exchange problem.

2. The method of claim 1, further comprising:
   for each inequality constraint:
      formulating the inequality constraint as an equality constraint comprising slack variables, wherein each slack variable is a binary variable; and
      determining the penalty term using the equality constraint comprising slack variables.

3. The method of claim 1, wherein when the quantum computing resource comprises a quantum annealing computer, optionally wherein the solution to the exchange problem is computed using quantum adiabatic computation.

4. The method of claim 1, wherein when the quantum computing resource comprises a gate-based universal quantum computer, optionally wherein the solution to the exchange problem is computed using a Quantum Approximate Optimization Approach or other quantum-classical hybrid variational algorithm.

5. The method of claim 1, further comprising performing classical post-processing of the data representing a solution to the exchange problem obtained from the quantum computing resource.

6. The method of claim 1, wherein initiating an action based on the obtained data representing a solution to the exchange problem comprises exchanging resources or services based on the solution to the exchange problem.

7. The method of claim 1, wherein the received data comprises data representing:
 exchange problem participants, wherein each participant offers resources or services in exchange for other resources or services without using a medium of exchange;
 constraints on exchanges between exchange problem participants; and
 the exchange problem.

8. The method of claim 7, wherein the exchange problem comprises a kidney exchange problem.

9. The method of claim 8, wherein the exchange problem participants comprise incompatible donor-recipient pairs, wherein each incompatible donor-recipient pair comprises (i) a donor willing to donate a kidney, and (ii) a patient in need of a donor kidney of a different type to that offered by the donor.

10. The method of claim 8, wherein constraints on exchanges between exchange problem participants comprise:
 a first constraint that ensures no kidney is donated more than once;
 a second constraint that ensures that a donor of an incompatible donor-recipient pair donates a kidney only if a patient in the incompatible donor-recipient pair receives a kidney from another donor.

11. The method of claim 8, further comprising:
 modelling the kidney exchange problem as a graph of vertices and directed weighted edges, wherein
 vertices represent incompatible donor-recipient pairs,
 edges represent compatible donor-recipient pairs; and
 edge weights represent a medical benefit of a compatible donor-recipient pair; and
 determining one or more disjoint cycles of donor-recipient pairs that increases overall medical benefits of associated kidney transplants.

12. The method of claim 11, wherein a number of donor-recipient pairs in each of the one or more disjoint cycles is below a predetermined threshold.

13. The method of claim 8, wherein initiating an action based on the obtained data representing a solution to the exchange problem comprises transplanting multiple kidneys based on the solution to the exchange problem.

14. A system comprising:
 a classical processor;
 a quantum computing device in data communication with the classical processor;
 wherein the classical processor and quantum computing device are configured to perform operations comprising:
  receiving data representing an exchange problem;
  determining, from the received data, an integer programming formulation of the exchange problem, the integer programming formulation of the exchange problem comprising: i) an objective function to be maximized, and ii) one or more constraints comprising equality and inequality constraints;
  mapping the integer programming formulation of the exchange problem to a quadratic unconstrained binary optimization (QUBO) formulation of the exchange problem, comprising:
   mapping the objective function to be maximized to a QUBO objective function to be minimized;
   determining a penalty term, comprising, for each equality constraint:
    representing the constraint as an equation equaling zero when the constraint is satisfied and equaling a strictly positive value when the constraint is not satisfied;
    multiplying the equation by a weight to generate a corresponding partial-penalty term; and
    including the generated partial-penalty terms in the penalty term; and
   adding the penalty term to the QUBO objective function to be minimized;
  obtaining data representing a solution to the exchange problem from a quantum computing resource; and
  initiating an action based on the obtained data representing a solution to the exchange problem.

15. The system of claim 14, further comprising:
 for each inequality constraint:
  formulating the inequality constraint as an equality constraint comprising slack variables, wherein each slack variable is a binary variable; and
  determining the penalty term using the equality constraint comprising slack variables.

16. The system of claim 14, wherein initiating an action based on the obtained data representing a solution to the exchange problem comprises exchanging resources or services based on the solution to the exchange problem.

17. The system of claim 14, wherein the received data comprises data representing:
 exchange problem participants, wherein each participant offers resources or services in exchange for other resources or services without using a medium of exchange;
 constraints on exchanges between exchange problem participants; and
 the exchange problem.

18. The system of claim 17, wherein the exchange problem comprises a kidney exchange problem.

* * * * *

UNITED STATES PATENT AND TRADEMARK OFFICE
CERTIFICATE OF CORRECTION

PATENT NO. : 10,592,816 B1
APPLICATION NO. : 16/399121
DATED : March 17, 2020
INVENTOR(S) : Kung-Chuan Hsu et al.

Page 1 of 1

It is certified that error appears in the above-identified patent and that said Letters Patent is hereby corrected as shown below:

On the Title Page

Item (56), Column 2 (OTHER PUBLICATIONS), Line 7, delete "graphos:" and insert -- graphs: --, therefor.

In the Specification

In Column 8, Line 27, delete "$w_{i,j} >> 0$" and insert -- $w_{i,j} > 0$ --.

In Column 10, Line 19, delete "$x^2 = x_i$" and insert -- $x_i^2 = x_i$ --.

In the Claims

In Column 16, Claim 1, Line 28, delete "minimized:" and insert -- minimized; --, therefor.

Signed and Sealed this
Second Day of June, 2020

Andrei Iancu
*Director of the United States Patent and Trademark Office*